Figure 1:
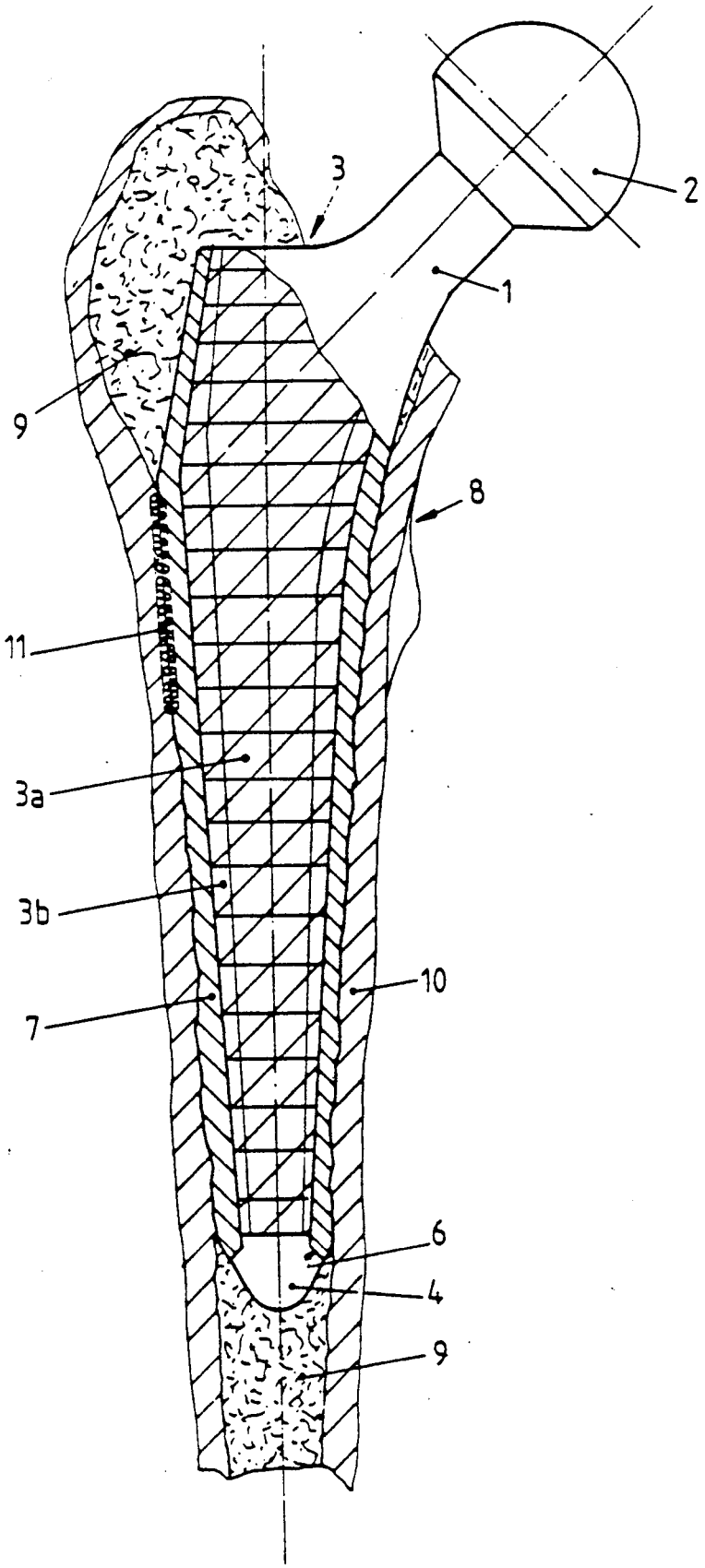

United States Patent [19]

Wintermantel et al.

[11] Patent Number: 5,037,442
[45] Date of Patent: Aug. 6, 1991

[54] FIXING STEM FOR A PROSTHESIS

[75] Inventors: Erich Wintermantel, Fislisbach; Manfred Flemming, Niederrohrdorf; Otto Frey, Winterthur, all of Switzerland

[73] Assignee: Sulzer Brothers Limited, Winterthur, Switzerland

[21] Appl. No.: 392,708

[22] Filed: Aug. 11, 1989

[30] Foreign Application Priority Data

Aug. 30, 1988 [CH] Switzerland ................... 3232/88

[51] Int. Cl.$^5$ ............................................. A61F 2/36
[52] U.S. Cl. ...................................... 623/23; 623/16; 623/18; 623/22; 433/173; 433/201.1
[58] Field of Search .................. 623/16, 18, 22, 23; 433/173, 201.1

[56] References Cited

U.S. PATENT DOCUMENTS

| | | | |
|---|---|---|---|
| 4,195,367 | 4/1980 | Kraus | 623/18 |
| 4,362,681 | 12/1982 | Spector et al. | 264/112 |
| 4,366,183 | 12/1982 | Ghommidh et al. | 623/16 |
| 4,506,681 | 3/1985 | Mundell | 623/16 |
| 4,532,660 | 8/1985 | Field | 623/23 |
| 4,562,598 | 1/1986 | Kranz | 623/18 |
| 4,570,271 | 2/1986 | Sump | 623/18 |
| 4,609,551 | 9/1986 | Caplan et al. | 623/16 |
| 4,750,905 | 6/1988 | Koeneman et al. | 623/23 |
| 4,778,474 | 10/1988 | Homsy | 623/16 |
| 4,812,120 | 3/1989 | Flanagan et al. | 433/173 |
| 4,904,534 | 2/1990 | Nagai | 433/201.1 |

FOREIGN PATENT DOCUMENTS

| | | |
|---|---|---|
| 0480221 | 5/1976 | Australia . |
| 0071658 | 2/1983 | European Pat. Off. ............. 623/16 |
| 0145339 | 7/1985 | European Pat. Off. . |
| 2425237 | 12/1979 | France . |
| 8704916 | 8/1987 | PCT Int'l Appl. . |
| 2045082 | 10/1980 | United Kingdom . |

Primary Examiner—Randall L. Green
Assistant Examiner—Stephanie L. Iantorno
Attorney, Agent, or Firm—Kenyon & Kenyon

[57] ABSTRACT

The stem of the endoprosthesis comprises a core which provides the necessary strength to the endoprosthesis and a jacket or sleeve of thermoplastic having a softening temperature below 60° C. The jacket can be made flowable upon heating so that during implantation, the jacket can be adapted to the bone cavity. In addition, the jacket can be heated at any subsequent time to return to a plastically deformable state in order to facilitate re-operations.

20 Claims, 2 Drawing Sheets

FIXING STEM FOR A PROSTHESIS

This invention relates to a fixing stem for a prosthesis. More particularly, this invention relates to a fixing stem for an endoprosthesis.

Heretofore, various types of fixing stems have been employed for implanting an endoprosthesis in a bone. For example, German OS 2 933 237 discloses a fixing stem embodied by a core of metal or fiber-reinforced plastics and a jacket or sleeve or the like also made of a fiber-reinforced plastics or of metal about the core. The purpose of this kind of construction is for the stem to have different strength properties over the length and/or cross-section.

German OS 2 636 644 describes endoprostheses devised from a combination of a biocompatible plastics, such as an acrylic resin or some other thermoplastic polymer, with a strengthening material, for example, a wide variety of fibers present, for example, as short fibers or endless filaments. The purpose of this combination is to provide the prosthesis with the necessary strength and to give the endoprosthesis a rigidity adapted to the bone material. For satisfactory adaptation to the bone and to minimize surface pressure, a stem of the endoprosthesis can be introduced into the bone while still soft and cured only after being placed in the bone, no particulars being given about this securing in the human body.

European Patent 0 074 981 describes a prosthesis whose stem is made at least to some extent of curable pre-preg material which cures only after introduction into a bone cavity after having been pressed by inflatable pressing means against the wall of the operation cavity. The purpose of this prosthesis is to adapt the shape of the stem to an individual surgically contrived cavity in the bone.

In all these constructions, there is irreversible curing of the plastics and so re-operation is impossible without some destruction of the prosthesis surface and/or of the growing bone material.

Other types of stem constructions have also been known which employ a polymer core and a polymer skin, such as described in WO87/04916. Likewise, stem constructions have been known to utilize stems which are coated on an external surface of plastic material, such as described in European Patent Application 0145339, U.K. Patent Application 2,045,082, U.S. Pat. No. 4,362,681, Australian Patent 480,221 and French Patent 2,339,388.

Stems have also been known which employ a wire mesh for implantation purposes, such as described in German O.S. 27 58 541.

It is an object of the invention to produce a prosthesis stem which can also be adapted to an individual bone and which permits re-operations without any risk of damage to prosthesis surface and/or the bone tissue.

It is another object of the invention to be able to remove an implanted endoprosthesis stem from a bone in a relatively easy manner.

Briefly, the invention provides a fixing stem for a prosthesis comprised of a rigid core and a thermoplastic jacket peripherally surrounding the core and having a softening temperature below a predetermined physiological critical value, for example in the range of from 45° C. to 60° C.

Materials which are suitable for the heat-softenable jacket include all such thermoplastic materials as have a softening range below a physiologically critical value. This value is approximately 60° C. although temperatures of up to 75° C. may be briefly permissible. Methacrylates, more particularly polyethylene methacrylate or polyisobutylene methacrylate, are preferred thermoplastics. Since the jacket and, in some circumstances, the core are made of polymerised plastics, the stem has the further advantage of not introducing any usually toxic monomers of the plastics into the human body.

The surgical procedure for implanting a prosthesis with a stem as described differs from the known procedure for implantation in a bone cement bed. In the present case, the jacket is part of the prosthesis and is already mounted on the core prior to introduction of the stem into the prepared bone cavity. For cementing, the cement is introduced as a separate substance into the bone cavity prior to implantation of the prosthesis. In that case, therefore, adhesion between the prosthesis and the bone cement occurs only after introduction into the bone. This adhesion is therefore subject to intra-surgical circumstances which may vary considerably between individual implantations.

In implantation, the stem, whose thickness is slightly over dimensioned relative to the bone cavity, is, for example, initially slightly heated and introduced into the bone cavity. In this state, plastically deformable surplus jacket material escapes to the entry aperture and can be removed. By further heating, for example, by means of a heating element or if the jacket and/or core are electrically conductive -by inductive heating, the jacket material is further warmed until becoming flowable and can be adapted to the wall surfaces of the bone cavity. Stabilization of the jacket and, where applicable, of the core if the core and jacket are made of the same plastics matrix material, is by simple cooling to body temperature, with simultaneous fixing of the prosthesis in the bone cavity. For re-operations, at least the jacket is reheated and therefore becomes flowable and can be removed from the bone with plastic deformation and without damage.

Advantageously, the range of softening temperatures for the jacket is between 45° and 60° C. If, as previously stated, the core and jacket are made of the same plastics, they differ from one another by their fiber reinforcement which, in the case of the core, is either long-fibered or of oriented short fibers while the jacket reinforcement, if any, is in the form of an irregular short fiber reinforcement.

If, as stated, the core and/or jacket are electrically conductive, the advantage is provided that they can be inductively heated relatively uniformly throughout their entire volume.

Another possibility is for the jacket to contain substances which stimulate bone growth and/or provided on at least some of the surface with structures which "retain" ongrowing tissue, such as braided or woven wire meshes embedded in the plastics of the jacket. The strengthening core can of course be made of metal in known manner.

Conveniently, for adaptation of the stem to the individual patient before the jacket is placed on the core, the shape and dimensions of the core are adapted by preliminary treatment at least substantially to the stem-receiving bone. In this event, the core can be, through the agency of different fiber densities and/or fiber orientations, devised non-uniformly from fiber-reinforced plastics with a central zone which receives substantially all the loading having and a surrounding mechanically workable shaping zone.

Also, implantation can be simplified if the distal end of the core has a non-softening closure element, for example, of titanium against which the jacket abuts.

Figure 2:
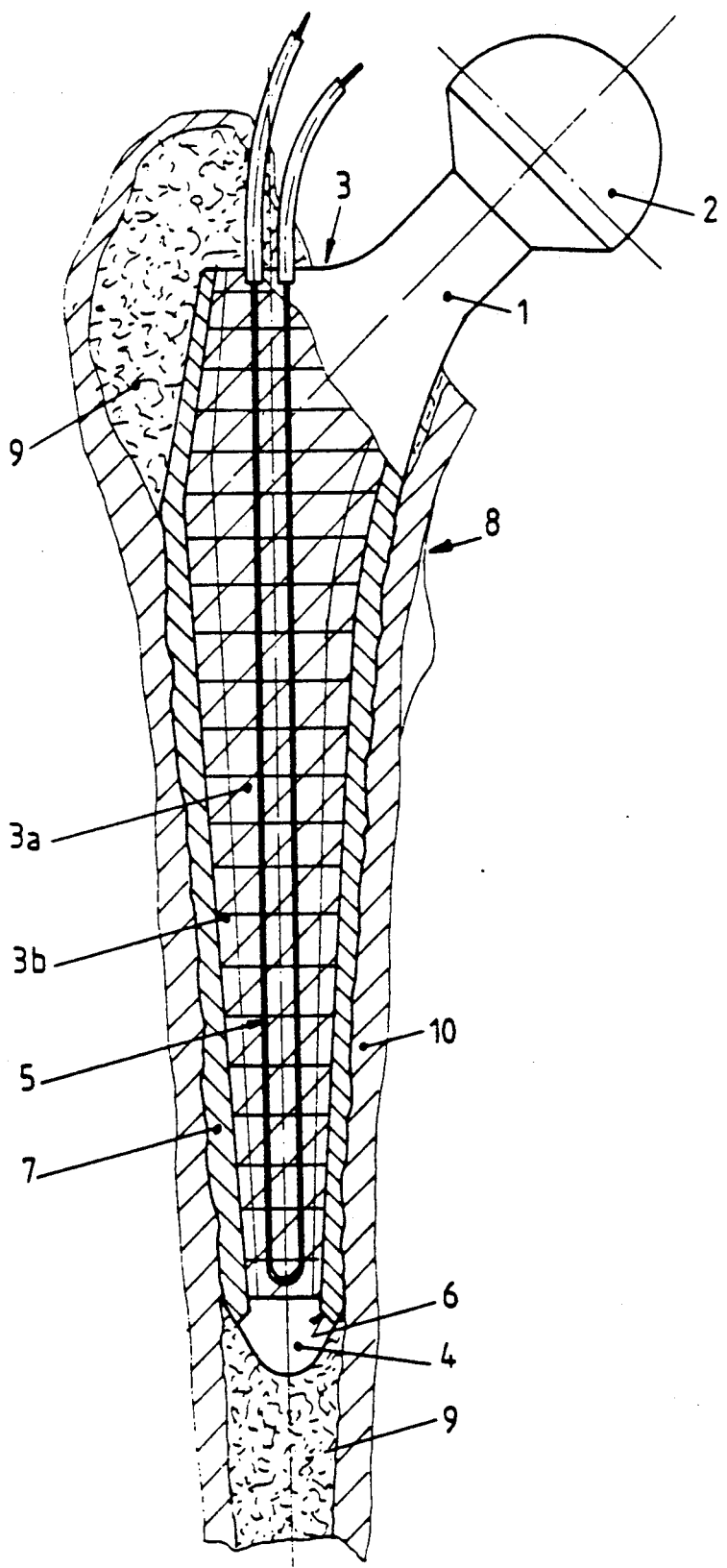

These and other objects and advantages of the invention will become more apparent from the following detailed description taken in conjunction with the accompanying drawings wherein:

FIG. 1 illustrates a cross sectional view of a stem in accordance with the invention implanted within a bone cavity of a femur; and FIG. 2 illustrates a view similar to FIG. 1 of a modified stem in accordance with the invention.

Referring to FIG. 1, the prosthesis in the form of a femoral head prosthesis which includes a neck 1 on which a joint head 2 is secured, for example, by means of a known conical pin connection. The head 2 is made of metal or ceramic while the neck 1 forms a part of a stem core 3. This core 3 is made of fiber-reinforced thermoplastic, for example polyisobutylene methacrylate reinforced by carbon fibers and adapted to the individual patient in shape and dimensions, for example by means of computer tomography photographs.

The core 3 is non-homogeneous with a non-uniform shape and has a strength-determining central zone 3a around which a mechanically treatable shaping zone 3b extends. The non-homogeneity is produced, for example, by different fiber densities, different fiber shapes, e.g. long fibers or short fibers and different fiber shape orientations, e.g. oriented or random.

In the present example, the central zone 3a contains continuous long fibers while the shaping zone 3b is strengthened by short fibers of from 1 to 5 millimeters in length and each of the same or different lengths, the latter fibers being oriented substantially along the stem longitudinal axis. To facilitate inductive heating of the stem, the fibers made of carbon or copper filaments are incorporated in the plastics matrix in addition to the fibers.

Referring to FIG. 2, wherein like reference characters indicate like parts as above, an electrical heating loop or spiral 5 can be provided in the central zone 3a with terminals for connection to a power supply led either out of the neck 1 (not shown) or by way of the proximal end of the prosthesis near the greater trochanter.

Referring to FIG. 1, the core 3 is closed in the distal zone by a closure element 4 which is not softenable and which is made, for example, of titanium. The closure element 4 has a peripheral heel or the like 6 on which the jacket 7 around the core 3 abuts.

The jacket 7 is also made of a thermoplastic but unlike the core 3, the jacket 7 may have if any, a reinforcement mace of short-fiber random carbon fibers, the density of said reinforcement being relatively reduced. The jacket 7 may be made electrically conductive by incorporating carbon fibers or copper filaments.

The stem is implanted in a femur 8 in whose spongy tissue 9 a corresponding cavity has been contrived surgically. As a result of heating and subsequent cooling, the jacket 7 has been adapted to the shape of the cavity, i.e. to the wall surface of the cortex 10 bounding the cavity so that an intimate contact is produced between the bone and the stem. To improve this bonding, parts of the jacket 7 have woven metal meshes 11 (FIG. 1) embedded to some extent in the jacket 7 so that bone tissue can, in known manner, invade the open pores of the meshes 11.

Also, the ongrowth of bone tissue on the jacket 7 can be promoted by bone-growth-stimulating substances such as, e.g. hydroxylapatit (HAP) which are added to the plastics matrix of the jacket 7.

When a core 3 is made of metal, for example, titanium, an adhesion between the jacket 7 and the core 3 is produced in the manner known for embedding implants in bone cements, to which end the metal core surface can have, for example, a surface-enlarging texture.

The invention thus provides a fixing stem for a prosthesis which can be readily implanted in a surgically prepared bone cavity and subsequentially removed without damage to the prosthesis stem and/or the bone cavity. The heat softenable characteristics of the jacket of the stem permit the stem to be heated so that the stem can be more particularly adapted to the wall surfaces of a bone cavity as well as to facilitate removal of the stem for a re-operation.

Adhesion of the plastic jacket to the core, of metal or of fibre reinforced materials nature, is defined by surface preparation of the core and by melting of the jacket. This bonding is comparable to gluing. Body fluids will not penetrate between jacket and core, any movement or deformation will occur within the jacket.

A reoperation procedure is performed in cases where loosening has occurred softening of the jacket will thus help to explant the prosthesis as the slip-out procedure will not be hindered by bone structures. The idea is to explant as much as possible from the prosthesis and to abrade bone only when surgical preparation for the new implantation is necessary in order to remove connective tissue which might be present due to the loosening process.

Hardening and softening of the jacket can be subsequently repeated during explantation so that a desired deformation of the implant can be achieved.

What is claimed is:

1. A fixing stem for a prosthesis comprising
a rigid core capable of being heated; and
a thermoplastic jacket peripherally surrounding said core and having a softening temperature below a predetermined physiological critical value and wherein said predetermined physiological critical value is less than or equal to 75° C. for softening upon heating of said core.

2. A fixing stem as set forth in claim 1 wherein said temperature is in the range of from 45° C. to 60° C.

3. A fixing stem as set forth in claim 1 wherein said jacket is of constant thickness.

4. A fixing stem as set forth in claim 1 wherein said core is made of fiber reinforced plastic.

5. A fixing stem as set forth in claim 4 wherein said core has a non-uniform shape including a central zone and a mechanically workable shaping zone about said central zone, each said zone having a different fiber density from the other zone.

6. A fixing stem as set forth in claim 1 wherein said core and said jacket are made of the same plastic.

7. A fixing stem as set forth in claim 1 wherein at least one of said core and said jacket is electrically conductive to permit electrical heating of said jacket to said softening temperature.

8. A fixing stem as set forth in claim 1 wherein said jacket contains a substance to stimulate bone ingrowth.

9. A fixing a stem as set forth in claim 1 which further comprises multilayer wire meshes in at least some zones of said jacket for bone ingrowth.

10. A fixing stem as set forth in claim 1 which further comprises a non-softening closure element at a distal end of said core abutting said jacket.

11. A fixing stem as set forth in claim 1 which further comprises an electrical heating loop disposed in said core for heating of said jacket.

12. A fixing stem for a prosthesis comprising
a rigid elongated core of fiber reinforced plastic; and
a thermoplastic jacket surrounding said core and having a softening temperature below a predetermined physiological critical value and wherein said predetermined physiological critical value is less than or equal to 75° C. for softening upon heating thereof during implantation in a bone.

13. A fixing stem as set forth in claim 12 wherein said temperature is in the range of from 45° C. to 60° C.

14. A fixing stem as set forth in claim 13 wherein said core has a non-uniform shape including a central zone and a mechanically workable shaping zone about said central zone, each said zone having a different fiber density from the other zone.

15. A fixing stem as set forth in claim 13 wherein at least one of said core and said jacket is electrically conductive to permit electrical heating of said jacket to said softening temperature.

16. A fixing stem as set forth in claim 13 which further comprises a non-softening closure element at a distal end of said core abutting said jacket.

17. A fixing stem for a prosthesis comprising
a rigid core of fiber reinforced plastic having an electrical heating loop herein for heating of said core; and
a thermoplastic jacket peripherally surrounding said core for heating by said core and having a softenable temperature in a range of from 45° C. to 60° C.

18. A fixing stem as set forth in claim 17 wherein said jacket is electrically conductive to permit electrical heating of said jacket to said softening temperature.

19. A fixing stem for a prosthesis comprising
a rigid elongated core of fiber reinforced plastic having at least one of carbon and copper filaments therein to be electrically conductive; and
a thermoplastic jacket surrounding said core and having a softening temperature below a predetermined physiological critical value and wherein said predetermined physiological critical value is less than or equal to 75° C., said jacket having at least one of carbon and copper filaments therein to be electrically conductive to permit electric heating of said jacket to said softening temperature.

20. A fixing stem as set forth in claim 19 wherein said temperature is in the range of from 45° C. to 60° C.

* * * * *

UNITED STATES PATENT AND TRADEMARK OFFICE
CERTIFICATE OF CORRECTION

PATENT NO. : 5,037,442
DATED : August 6, 1991
INVENTOR(S) : Erich WINTERMANTEL, et al.

It is certified that error appears in the above-identified patent and that said Letters Patent is hereby corrected as shown below:

Col. 2, line 30, change "or" to --or--. (1st occurrence).

Col. 3, line 56, change "mace" to --made--.

Col. 4, line 29, change "occurred" to --occurred,--.

Col. 6, line 6, change "herein" to --therein--.

Signed and Sealed this

Fifteenth Day of June, 1993

Attest:

MICHAEL K. KIRK

Attesting Officer     Acting Commissioner of Patents and Trademarks